United States Patent [19]

Hertl et al.

[11] 4,311,687

[45] Jan. 19, 1982

[54] RADIOMETRIC ASSAY OF DIALYSATES

[75] Inventors: William Hertl, Corning; Gerald Odstrchel, Horseheads, both of N.Y.

[73] Assignee: Corning Glass Works, Corning, N.Y.

[21] Appl. No.: 90,535

[22] Filed: Nov. 2, 1979

Related U.S. Application Data

[63] Continuation-in-part of Ser. No. 940,702, Sep. 8, 1978, abandoned.

[51] Int. Cl.³ .................... G01N 33/54; G01N 33/60; G01T 1/00
[52] U.S. Cl. .................................... 424/1; 23/230 B; 424/12
[58] Field of Search ............................ 424/1, 1.5, 12; 23/230 B

[56] References Cited

U.S. PATENT DOCUMENTS

| | | | |
|---|---|---|---|
| 3,843,444 | 10/1974 | Likhite | 424/12 |
| 3,981,981 | 9/1976 | Reunanen | 424/1.5 |
| 4,235,865 | 11/1980 | Thoma | 424/1 |
| 4,255,411 | 3/1981 | Lim et al. | 424/1 |

*Primary Examiner*—Christine M. Nucker
*Attorney, Agent, or Firm*—William E. Maycock

[57] ABSTRACT

An improved radiometric assay of dialysates from equilibrium dialysis procedures which involves using immobilized antibody specific for a given hapten to separate free hapten (including radiolabeled hapten) from radiolabeled non-hapten breakdown products.

4 Claims, No Drawings

RADIOMETRIC ASSAY OF DIALYSATES

CROSS-REFERENCE TO RELATED APPLICATION

This is a continuation-in-part of application Ser. No. 940,702, filed Sept. 8, 1978, now abandoned.

BACKGROUND OF THE INVENTION

Equilibrium dialysis is a procedure for measuring the concentration of free, relatively small molecules in a sample. The procedure originally was designed to study the quantitative aspects of immunity reactions, and in particular to study the combination of antibodies with simple haptens. See J. Marrack and F. C. Smith, *Brit. J. Exptl. Path.*, 13, 394 (1932). Over the years, the procedure has been employed primarily in immunological studies; see, e.g., F. Haurowitz and F. Breinl, *Z. Physiol. Chem.*, 214, 111 (1933); H. N. Eisen and F. Karush, *J. Am. Chem. Soc.*, 71, 363 (1949); and D. N. Weir, Editor, "Handbook of Experimental Immunology," Second Edition, Blackwell Scientific Publications, Oxford, 1973, pages 16.1–16.21.

In principle, equilibrium dialysis can be employed to determine the concentration of any relatively small molecule in a given sample; the only requirement is that the material to be measured must pass freely through a semi-permeable membrane. Once equilibrium has been achieved, it is only necessary to analyze the dialysate for the desired material.

As a practical matter, equilibrium dialysis appears to be directed primarily to the determination of the concentration of free or unbound haptens which are present in blood serum or plasma samples. Thus, the discussion herein will be directed toward that end-use, although it should be apparent that the invention disclosed herein is not to be limited by such discussion. Furthermore, for simplicity the discussion will be limited to the assay of free thyroxine ($T_4$) in blood serum or plasma.

It should be noted that the need for equilibrium dialysis in such a determination arises because a large proportion of the hapten is bound to much larger molecules, such as serum proteins, which do not pass through a semi-permeable membrane. The free or unbound portion of the hapten is the physiologically important quantity, which renders such quantity clinically important, as well.

At the present time, the only generally-accepted reference method for measuring the concentration of free thyroxine in blood serum or plasma samples is by equilibrium dialysis. Basically, the procedure involves placing the serum sample in a dialysis bag along with radiolabeled thyroxine. The bag is placed in a known volume of liquid and typically incubated for 16 hours. At the end of the incubation period, a sample of the dialysate is taken and the radioactivity of such sample is measured. In practice, however, it also is necessary to go through a procedure to remove radioactive breakdown products from the dialysate. Such procedure involves adding to the dialysate pooled human serum to absorb free thyroxine. A resin then is added to absorb the radioactive breakdown products, which resin subsequently is removed from the dialysate. Unfortunately, the resin addition step is extremely critical. If the resin is in the dialysate for too short a time, it will not pick up all of the breakdown products, thereby leading to erroneously high results. Conversely, if the resin is in contact with the dialysate for too long a time, it also strips free thryoxine from the added serum protein, leading to erroneously low results. Thus, it is necessary to critically control the time and conditions of the resin addition and removal steps in order to obtain correct results.

SUMMARY OF THE INVENTION

Accordingly, the present invention relates to an improved radiometric assay of dialysates obtained from equilibrium dialysis. More particularly, the present invention relates to a method which eliminates the prior-art use of resin to remove radioactive breakdown from the dialysate.

Thus, the present invention provides, in a method for determining the concentration of a free or unbound hapten in a liquid sample, which method is based on equilibrium dialysis and which comprises the steps of:

A. adding a radiolabeled hapten to the liquid sample;
B. dialysing the mixture resulting from step A;
C. separating the free hapten in the dialysate from radiolabeled nonhapten entities by absorbing such entities on a solid-phase material which is added to the dialysate;
D. removing such solid-phase material from the dialysate; and
E. measuring the amount of radiolabeled hapten in the dialysate; the improvement which comprises replacing steps C, D and E with the following new steps, C', D' and E';
C'. adding to the dialysate an immobilized antibody in an amount sufficient to complex with all hapten which has dialyzed, in which the antibody is specific for the hapten;
D'. separating the resulting immobilized antibody-hapten complex from the dialysate; and
E'. measuring the amount of radiolabeled hapten present in the immobilized antibody-hapten complex.

As already indicated, equilibrium dialysis is particularly useful for determining the concentration of free hapten in a liquid sample. The procedure is especially useful for determining the concentration of free thryoxine in blood serum or plasma samples. Such determination, of course, is part of the hemotological examination which is routinely employed in the prophylaxis and therapy of a variety of disorders and diseases.

DETAILED DESCRIPTION OF THE INVENTION

As used herein, the term "hapten" is meant to include any relatively small molecule which is capable of passing through a semi-permeable membrane and for which a specific antibody can be generated in accordance with well known procedures. Examples of suitable haptens include, among others, thyroxine ($T_4$); triiodothyronine ($T_3$); dilantin; corticosteroids, such as deoxycorticosterone, 17-hydroxydeoxycorticosterone (deoxycortisol), corticosterone, 17-hydroxycorticosterone (cortisol or hydrocortisone), 11-dehydrocorticosterone, 17-hydroxy-11-dehydrocorticosterone (cortisone), and aldosterone; other steroids, such as progesterone, estrone, estradiol, estriol, cholesterol, cholestanol, vitamin $D_2$, and vitamin $D_3$; vitamin $D_{12}$; folic acid; drugs; mescaline; lysergic acid diethylamide; 8-anilino-1-naphthalenesulfonic acid; diphosphopyridine nucleotide derivatives; amino acids; enzyme inhibitors; and the like.

In its simplest form, the present invention involves adding a quantity of an immobilized antibody to an aliquot of the dialysate from an equilibrium dialysis procedure. The resulting mixture then is centrifuged and the supernatant liquid discarded. The immobilized antibody which remains has complexed thereto the hapten which is the subject of the assay. The radioactivity of the immobilized antibody-hapten complex is counted and the free hapten determined in accordance with well-known procedures.

It will be appreciated by those having ordinary skill in the art that additional procedures may be required, depending upon the nature of the hapten. For example, the assay for free thyroxine in blood serum or plasma requires the addition of some pooled human serum or other protein in order to minimize nonspecific absorption of thyroxine on the glass wall of the dialysis flask. Furthermore, a deblocking agent, such as thimerosal (merthiolate), often is employed in order to prevent absorption of thyroxine by the added human serum. Alternatively, one may employ coated flasks or vessels in order to prevent nonspecific absorption.

In general, the immobilized antibody is prepared in accordance with methods which are well known in the art. While essentially any water-insoluble carrier can be employed, the preferred carriers are water-insoluble inorganic materials having available surface oxide or hydroxy groups. Such inorganic materials may be classified in terms of chemical composition as siliceous materials or nonsiliceous metal oxides. Of the siliceous materials, a preferred carrier is porous glass. Other siliceous inorganic carriers include colloidal silica, wollastonite, silica gel, and bentonite. Representative nonsiliceous metal oxides include alumina, hydroxy apatite, and nickel oxide. Of the foregoing, siliceous materials are preferred with glass being most preferred. While it is not essential to the present invention, porous carriers are preferred in order to maximize the amount of antibody which can be immobilized on the carrier. An especially suitable carrier is a suspendable porous glass such as that disclosed in U.S. Pat. No. 4,052,010.

In general, the antibodies can be coupled to the carrier by any known method. A particularly suitable procedure, however, involves coupling the antibody by means of a silanized carrier which then is derivatized by N-hydroxysuccinimide to give carrier which is ready for binding to the antibody. The silanization of inorganic carriers is disclosed in, e.g., U.S. Pat. Nos. 3,652,761, 3,519,538, and 3,669,841. For an example of the preparation of immobilized antibody using the N-hydroxysuccinimide technique, see U.S. Pat. No. 4,034,073.

The present invention is further illustrated, but not limited, by the example which follow. In the examples, the immobilized antibody was stored as a slurry and measurements of antibody consequently were by volume. The immobilized antibody slurry was prepared as already described. In general, 100 mg. of porous glass carrier having antibody attached thereto corresponds approximately to a fourfold excess of antibody over the amount of free thryoxine which is estimated to be present in the serum. Such fourfold excess insures complete binding of free thyroxine in the sample. Typically, 100 mg. of carrier having antibody attached thereto was present in 0.5 ml of the immobilized antibody slurry or suspension.

The protocols employed for the prior-art free thyroxine determination and the free thryoxine determination employing the improved radiometric assay described and claimed herein are as follows:

Reagents

A. Phosphate buffer at pH 7.4 was prepared by dissolving 12.8 grams of disodium hydrogen phosphate and 6.62 grams of sodium dihydrogen phosphate in distilled water and diluting the resulting solution to one liter.

B. The resin employed in the prior-art free thyroxine determination was Rexyn 201 anion exchange resin, 16–50 mesh, obtained from Fisher Scientific Company, Pittsburgh, Pa. The resin was washed 6 or 7 times with distilled water and isolated by filtration in a Buchner funnel using Whatman No. 1 filter paper. The resin was dried in shallow trays at 70°–80° C.

C. Normal pooled human serum was obtained from the Arnot-Ogden Hospital, Elmira, N.Y.

D. Thyroxine labeled with $I^{125}$ having a specific activity of about 100 $\mu C/\mu g$, was obtained from Nuclear Corp., St. Louis, Mo.

Purification of Labeled Thyroxine

To purify sufficient labeled thyroxine for about 25 samples in duplicate, approximately 45 $\mu C$ of $I^{125}$ thyroxine is required. The volume of labeled thyroxine solution employed is determined in the usual manner, based on the concentration of labeled thyroxine in the solution and the decay factor. Thus, the calculated volume of labeled thyroxine solution is added to 1.5 ml. of distilled water and 4.5 ml. of pooled normal serum. The resulting mixture is agitated gently. After about 15 minutes at ambient temperature, 200 mg. of Rexyn 201 is added and the resulting mixture is vortexed for one minute. The resin is allowed to settle, and the purified labeled thyroxine solution is transferred to another vessel.

Procedure

To 0.7 ml. of serum sample is added 0.1 ml. of the purified $I^{125}$ thyroxine solution. The resulting mixture is vortexed and then allowed to stand for about 10 minutes. As a check, 0.1 ml. of the serum-labeled thyroxine solution is transferred to another vessel and total counts are obtained. The number of counts per minute from such 0.1 ml. sample should be approximately 100,000. A 0.5 ml. aliquot of the remaining serum-labeled thyroxine solution is transferred to dialysis tubing which has been conditioned in distilled water. The tubing is sealed and placed in 9 ml. of phosphate buffer in a 25-ml. Erlenmeyer flask. The vessel is stoppered, placed in a shaker water bath at 37° C., and agitated overnight or for about 16 hours at about 100 strokes per minute. The vessel then is allowed to come to room temperature, and the dialysis tubing is removed and discarded.

A. Prior Art Procedure.

To each dialysate is added 0.5 ml. of pooled normal serum. The flask is mixed gently and allowed to stand for about 10 minutes. To each flask then is added approximately 600 mg. of Rexyn 201 resin. The flask is stoppered and vigorously shaken in a water bath for 1.5 minutes. The resin then is allowed to settle and the supernatant liquid is removed by decantation. A 2.0-ml. aliquot of the supernatant liquid is transferred to a separate vessel and counted.

B. Improved Radiometric Assay of the Present Invention

To the dialysate is added 0.5 ml. of pooled human serum. The resulting mixture is allowed to stand at ambient temperature for about 20 minutes. A 2.0 ml. aliquot of the dialysate is transferred to a separate vessel, to which then is added 0.5 ml. of immobilized antibody suspension and 0.5 ml. of a stock thimerosal solution which is prepared by dissolving 1.75 g. of thimerosal in 50 ml. of 0.03 M phosphate buffer containing 0.1% bovine serum albumin. The resulting mixture is vortexed and allowed to stand at room temperature for 1.5-2 hours. The mixture then is centrifuged, the supernatant liquid discarded, and the pellet counted.

EXAMPLE 1

Table I gives the results obtained by running replicate samples of a pooled human serum which previously had been measured by the conventional, prior-art method. The value of free thyroxine was determined by such conventional method to be 1.6±0.2 ng. per 100 ml.

TABLE I

Free Thyroxine Values of Pooled Normal Human Serum with Varying Amounts of Immobilized Antibody

| Amount Immobilized Antibody Added, ml. | Free $T_4$, ng/100 ml. | Free $T_4$ Ave. |
|---|---|---|
| 0.1 | 1.39 | 1.52 |
|  | 1.65 |  |
| 0.2 | 1.54 | 1.64 |
|  | 1.75 |  |
| 0.5 | 1.69 | 1.74 |
|  | 1.79 |  |
| 1.0 | 1.67 | 1.74 |
|  | 1.82 |  |

Overall Average: 1.66

From the above table, it is seen that the method of the present invention provides excellent agreement with the results obtained by the prior art method, provided that sufficient antibody is present. It will be apparent to those having ordinary skill in the art that several preruns may be required in order to determine the optimum amount of antibody and other conditions.

EXAMPLE 2

Table II gives a comparison of results obtained using serum samples having a wide range of free thryoxine values. From the table, it is apparent again that there is excellent agreement with the conventional method, regardless of the level of free thyroxine which is present in the serum sample.

TABLE II

Comparison of Free Thyroxine Values in Human Serum Samples Determined by Conventional Method and Method of Present Invention

| Free $T_4$, Conventional Method, ng./100 ml. | Free $T_4$ Using Immobilized Antibody, ng./100 ml. |
|---|---|
| 1.6 | 1.7 |
| 1.6 | 1.5 |
| 7.5 | 7.6 |
| 7.5 | 6.1 |
| >6 | 9.5 |
| >6 | 10.1 |
| 0.5 | 0.6 |
| 0.5 | 0.5 |
| 0.7 | 0.6 |
| 0.7 | 0.6 |
| 1.2 | 1.3 |
| 1.2 | 1.2 |
| 1.6 | 1.8 |
| 1.6 | 1.7 |
| 7.8 | 6.4 |
| 7.8 | 6.5 |
| >6 | 7.6 |
| >6 | 7.5 |
| 0.6 | 0.7 |
| 0.6 | 0.6 |
| 0.5 | 0.5 |
| 1.3 | 1.5 |
| 1.3 | 1.3 |

We claim:

1. In a method for determining the concentration of a free or unbound hapten in a liquid sample, which method is based on equilibrium dialysis and which comprises the steps of:
   A. adding a radiolabeled hapten to the liquid sample;
   B. dialysing the mixture resulting from step A;
   C. separating the free hapten in the dialysate from radiolabeled nonhapten entities by absorbing such entities on a solid-phase material which is added to the dialysate;
   D. removing such solid-phase material from the dialysate; and
   E. measuring the amount of radiolabeled hapten in the dialysate; the improvement which comprises replacing steps C, D, and E with the following new steps, C', D', and E':
   C'. adding to the dialysate an immobilized antibody in an amount sufficient to complex with all hapten which has dialyzed, in which the antibody is specific for the hapten;
   D'. separating the resulting immobilized antibody-hapten complex from the dialysate; and
   E'. measuring the amount of radiolabeled hapten present in the immobilized antibody-hapten complex.

2. The method of claim 1 in which the liquid sample is blood serum or plasma.

3. The method of claim 2 in which the hapten is thyroxine.

4. The method of claim 2 in which the hapten is triiodothyronine.

* * * * *